Jan. 20, 1976
M. TANTAU
ROSE PLANT
Filed Sept. 16, 1974
Plant Pat. 3,824
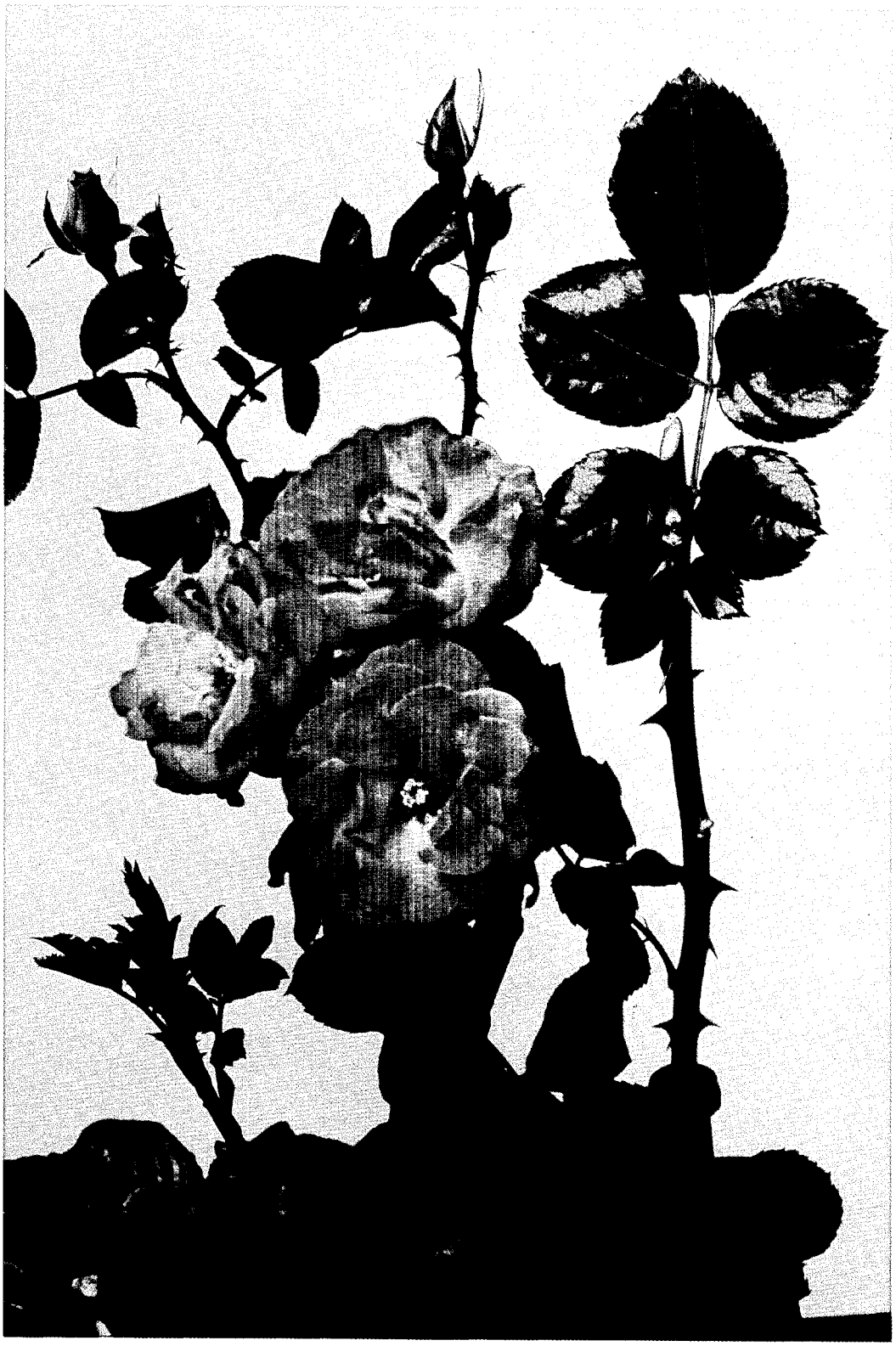

United States Patent

Plant Pat. 3,824

Patented Jan. 20, 1976

1

3,824

ROSE PLANT

Mathias Tantau, Utersen, Germany, assignor to Jackson & Perkins Company, Medford, Oreg.

Filed Sept. 16, 1974, Ser. No. 506,755

Int. Cl. A01h *5/00*

U.S. Cl. Plt.—28 1 Claim

This invention relates to a new and distinct cultivar of rose plant of the floribunda class originated by crossing the cultivar Dream Waltz, unpatented, with pollen from the cultivar Europeana, U.S. Plant Pat. 2,540.

The primary objective of this breeding was to produce a new and distinct cultivar of the floribunda class with a compact type of plant bearing large blooms of a color more closely resembling scarlet than blooms of Europeana whose flower color is more crimson.

This objective was fully achieved along with other desirable improvements as evidenced by the following unique combination of characteristics which are outstanding in the new cultivar and which distinguish it from its parents as well as from all other cultivars of which I am aware:

1. A densely growing compact plant.
2. Large, abundant foliage.
3. An orange red flower color as compared to a flower color in Europeana of Chrysanthemum Crimson on the upper side of the petals.
4. A similarity in appearance of the plant habit to Europenana but usually growing in a more upright manner.

Asexual reproduction of my new cultivar by budding as performed at Utersen, W. Germany, shows that the aforementioned characteristics and distinctions come true to form and are established and transmitted through succeeding propagations.

The accompanying illustration shows typical specimens of the vegative growth and flowers of my cultivar in different stages of development and as depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
- *Seed Parent.*—Dream Waltz.
- *Pollen Parent.*—Europeana.

Classification:
- *Botanic.*—Rosa hybrid.
- *Commercial.*—Floribunda.

FLOWER

Observations were made at Tustin, Calif. in August 1974.

Blooming habit: Recurrent—continuous.

Bud:
- *Size.*—Medium.
- *Form.*—Pointed.
- *Color.*—When sepals first divide: Wilson's Orient Red 819. When half blown; inside of petals Orient Red 819/3; reverse of petals Orient Red 819/3.
- *Receptacle.*—Color: light green. Shape: funnel. Size: broad. Surface: smooth.
- *Peduncle.*—Length: short. Surface: smooth. Color: medium green. Strength: erect.
- *Opening.*—Petals dropped.

Bloom:
- *Size.*—Medium, 3–5" when fully expanded.
- *Borne.*—Several together, if in clusters, rounded.

2

- *Stems.*—Long, normal strength.
- *Form.*—When first open—flat. Permanence—retains its form to the end.
- *Petalage.*—Number of petals under normal conditions. 22:26.
- *Color.* — Center of flower: Upper side of petals Orient Red 819/3; reverse side of petals Turkey Red 721/3. Outer petals: upper side of petals Orient Red 819/3; reverse of petals Turkey Red 721/3. Base of petals, small near-white area. General tonality from a distance Orient Red 819/3. Variegations—none.
- *Discoloration.* — General tonality at end of first day—Orient Red 819/3. Third day—Orient Red 819/3.
- *Fragrance.*—None.
- *Petals.*—Texture: Thick. Surface: Shiny, inside; reverse—satiny.
- *Shape.*—Oval.
- *Form.*—Flat.
- *Arrangement.*—Imbricated.
- *Petaloids in center.*—Few, small.
- *Persistence.*—Drop off cleanly.
- *Lastingness.*—On the plant—very long. As a cut flower—short.

Reproductive parts:
- *Anthers.* — Medium, many. Color—white, yellow. Arrangement—regular around styles.
- *Filaments.*—Short. Color—yellow, brown.
- *Pollen.*—Gold yellow.
- *Styles.*—Bunches, of uneven medium length.
- *Stigmas.*—Yellow, red.
- *Ovaries.*—All enclosed in calyx.

Fruit:
- *Form.*—Round.
- *Surface.*—Smooth.
- *Color at maturity.*—Orange-Scarlet Red.
- *Sepals.*—Recurved.

Plant:
- *Form.*—Bush.
- *Growth.*—Very vigorous, upright, compact.

Foliage:
- *Size.*—Large.
- *Quantity.*—Abundant.
- *Color.*—New foliage: Reddish. Old foliage: Spinach Green 0960. Number of leaflets on normal mid-stem leaves 5–7.

Leaflets:
- *Shape.*—Oval pointed.
- *Texture.* — Upper side — Leathery. Under side—Rough. Ribs and veins: Ordinary.
- *Edge.*—Serrated.
- *Serration.*—Single, sharp.
- *Petiole.*—Rachis — Color — Green. Underside—Prickles.
- *Stipules.*—Medium, serrated.
- *Disease resistance.*—Resistant to mildew and black-spot under normal growing conditions at Utersen, Germany.

Wood:
- *New wood.*—Color—Reddish.
- *Bark.*—Smooth.
- *Old wood.*—Color—Green.
- *Bark.*—Smooth.

Thorns:
- *Quantity.*—On main stalks from base—Many. On laterals from stalk—Ordinary.
- *Form.*—Narrow base.
- *Position.*—Irregular.

Prickles:

*Quantity.*—On main stalks—Few. On laterals—Few.

*Color.*—Brown.

Short needles:

*Quantity.*—On main stalks—Few. On laterals—Few.

Notes:

*Marks of identification.*—Very shiny red blossom color which didn't change with very leathery and shiny, large foliage.

I claim:

1. A new and distinct cultivar of rose of the floribunda class, substantially as herein shown and described, characterized particularly as to novelty by the unique combination of a vigorous, compact plant habit, abundant, large foliage, an orange red flower color.

No references cited.

ROBERT E. BAGWILL, Primary Examiner